US00PP11545P

United States Patent [19]

Kotobuki et al.

[11] Patent Number: Plant 11,545

[45] Date of Patent: Oct. 3, 2000

[54] JAPANESE PEAR TREE NAMED 'KOTOBUKI SHINSUI'

[75] Inventors: Kazuo Kotobuki, Tsukuba; Tetsuo Masuda, Morioka; Toji Yoshioka, Ibaraki; Minoru Nagara, Kurayoshi; Masato Uchida, Tottori; Kosuke Inoue, Tottori; Kenji Murata, Tottori; Kenichi Kitagawa, Tottori, all of Japan

[73] Assignee: National Institute of Agrobiological Resources Ministry of Agriculture, Forestry and Fisheries, Tsukuba, Japan

[21] Appl. No.: 09/035,103

[22] Filed: Mar. 5, 1998

[51] Int. Cl.[7] ..... A01H 5/00

[52] U.S. Cl. ..... Plt./178

[58] Field of Search ..... Plt./178, 176

[56] References Cited

U.S. PATENT DOCUMENTS

P.P. 7,758 12/1991 Machida et al. ..... Plt./176

P.P. 8,529 1/1994 Nishida et al. ..... Plt./176

OTHER PUBLICATIONS

Kotobuki, K, New Japanese Pear Cultivar 'Kotobuki Shinsui' Institute of Radiation Breeding, NIAR319–322, 1997.

Kotobuki, K. "Gold Nijiseiki", a new Japanese pear mutant cultivar to black spot disease induced by chronic irradiation of gamma rays, Reprinted from the Bulletin of the National Institute of Agrobiological Resources (Japan) No. 7 (Mar. 1992).

*Primary Examiner*—Howard J. Locker
*Assistant Examiner*—Wendy A Baker
*Attorney, Agent, or Firm*—Arent Fox Kintner Plotkin & Kahn, PLLC

[57] ABSTRACT

The new and distinct cultivar relates to a russet type Japanese pear tree that has a strong resistance to black spot disease and has substantially the same excellent qualities as the Japanese pear cultivar 'Shinsui'. The new pear tree bears a yellowish brown fruit, is highly sweet, medium in acidity, and has a rich taste that is suitable for dessert use.

12 Drawing Sheets

BACKGROUND OF THE INVENTION

The present invention relates to a new and distinct cultivar of Japanese pear tree (*Pyrus pyrifolia*), and particularly to a russet type pear tree having characteristics substantially the same as those of 'Shinsui' (unpatented in the U.S.), but having a significantly strong resistance to black spot disease.

In Japan, 'Shinsui', which was obtained from the crossing of 'Kikusui' (seed parent)(unpatented in the U.S.) and 'Kimizuka Wase' (pollen parent)(unpatented in the U.S.) and was released in 1965, is a popular cultivar. The fruit of 'Shinsui' ripens and can be eaten 7 to 10 days earlier than that of 'Kosui' (unpatented in the U.S.), and the taste of the fruit is sweet and rich. It has, however, a shortcoming in that 'Shinsui' is susceptible to black spot disease. Black spot disease develops in the leaves, stems and fruits of the 'Shinsui' tree. In particular, the young fruit is associated with the formation of black and rounded lesions and cracks. It is necessary to take care that 'Shinsui' not be infected with the disease, thus, 'Shinsui' is gradually decreasing in popularity. One object of the present invention is to provide an improved cultivar of the pear fruit tree having a strong resistance to black spot disease, while also having the excellent characteristics of the 'Shinsui' cultivar.

ORIGIN AND A SEXUAL REPRODUCTION OF THE CULTIVAR

The new cultivar of Japanese pear tree was derived from 'Shinsui' by mutation breeding. Since 1987, many scions of 'Shinsui' were exposed to γ-rays and the scions were top-grafted on mature trees. Leaves of grown vegetative shoots were tested using crude toxin of black spot disease, i.e., AK toxin. In 1989, among the scions exposed to γ-rays at a rate of 2.5 Gy/hour for a total radiation dose of 80Gy, one of the scions having a distinctively stronger resistance to black spot disease than the original cultivar 'Shinsui' was found. It has been confirmed that the variant grown from the scion has a significantly stronger resistance to black spot disease than 'Shinsui'. Branches of the new variant were grafted on rootstocks of the variety 'Hakko' and/or top-grafted on mature trees to study their characteristics such as vigor in the field.

As the trees bore fruits for the first time in 1991, the fruit characteristics were studied. Since then, is has been determined that the trees of the new variety have a significantly stronger resistance to black spot disease than 'Shinsui', while also displaying the excellent characteristics of 'Shinsui'. For instance, the trees of 'KOTOBUKI SHINSUI' had only slight lesions of black spot disease on the shoots and young fruit; little or no defoliation or abscission of fruit due to black spot disease infection was observed in filed tests. Meanwhile, 'Shinsui' had developed lesions due to black spot disease infection on the shoots and young fruit and defoliation or abscission of fruit was observed in plants cultivated without bagging.

This new and distinct cultivar of Japanese pear tree was asexually reproduced by grafting at the various Prefectural Experimental Stations (Tsukuba-shi, Ibaraki-ken; Kuki-shi, Saitama-ken; Chiba-shi, Chiba-ken; Takamori-machi, Shimoina-gun, Nagano-ken, and Daiei-cho, Tohaku-gun, Tottori-ken), and the homogeneity and stability thereof was confirmed. The new cultivar was named 'KOTOBUKI SHINSUI'.

The new cultivar of Japanese pear tree according to the present invention was developed from 'Shinsui' by mutation breeding using γ-rays as a mutagen. As described above, 'Shinsui', the parent cultivar, was obtained from the crossing of 'Kikusui' and 'Kimizuka Wase' and is widely cultivated in Japan. The main characteristics of 'Shinsui' that differ from the instant cultivar are as follows:

Tree:

*Vigor.*—New shoot growth averaged 183 cm in 1999.

*Spurs.*—In 1999, and average of 15.1 per meter of a branch.

Branches (shoot):

*Length of internode.*—Short, about 3.9 cm.

Leaves:

*Size.*—Medium (12.6 cm long by 7.6 cm wide).

Flowers:

*Number of petals.*—Slightly more than medium, 5.1 per flower on average.

*Number of stamens.*—Slightly more than medium, 27.0 on average.

*Amount of pollen.*—High.

Fruit:

*Size.*—Small, 319 g on average in 1992.

*Size of core.*—Ratio of transverse diameter of core to transverse diameter of fruit is medium, 24.9/84.2.

*Taste.*—Sugar content of juice, about 13.8%; medium acidity, pH 4.7; no astringency.

*Maturity.*—Ripening early in the season, e.g., August 15th–24th at the Tottori Prefecture, Japan.

Resistance to Diseases: Has a susceptibility to black spot disease and has minor susceptibility to pear scab, pear canker and *Physalospora canker.* The tree is not susceptible to pear necrotic spot virus. The cultivar 'Shinsui' is widely cultivated, and its nursery stock is easily available in Japan.

SUMMARY OF THE INVENTION

The characteristics of the new cultivar of Japanese pear tree 'KOTOBUKI SHINSUI' are substantially the same as those of 'Shinsui', with the exception of those enumerated above and the additional exception that 'KOTOBUKI SHINSUI' has an obviously stronger resistance to black spot disease than 'Shinsui'. The new cultivar can be cultivated under the same controls as 'Kosui' or 'Hosui' (unpatented in the U.S.), which are both resistant to black spot disease.

The new cultivar has strong vigor. The shoots are dark brown. Although the new cultivar has few axillary flower buds and many spurs, the spurs have a tendency to be blind buds. The flower buds are oval in shape and brown in color.

Flowering time is a little earlier than that of 'Kosui'. The flowers have less petals than those of 'Kosui' and the color of the anthers is deep red, deeper than those of 'Kosui'.

The fruit size is small (about 250–300 g). The fruit is oblate and the uniformity of the fruits is good. The color of the fruit skin is yellowish brown. The flesh is yellowish white and is more yellowish than the flesh of 'Kosui' in color and slightly softer and rougher in texture. The sugar content of the fruit is about 13.6%, slightly higher than that of 'Kosui'.

DESCRIPTION OF THE INVENTION

Figure 1:
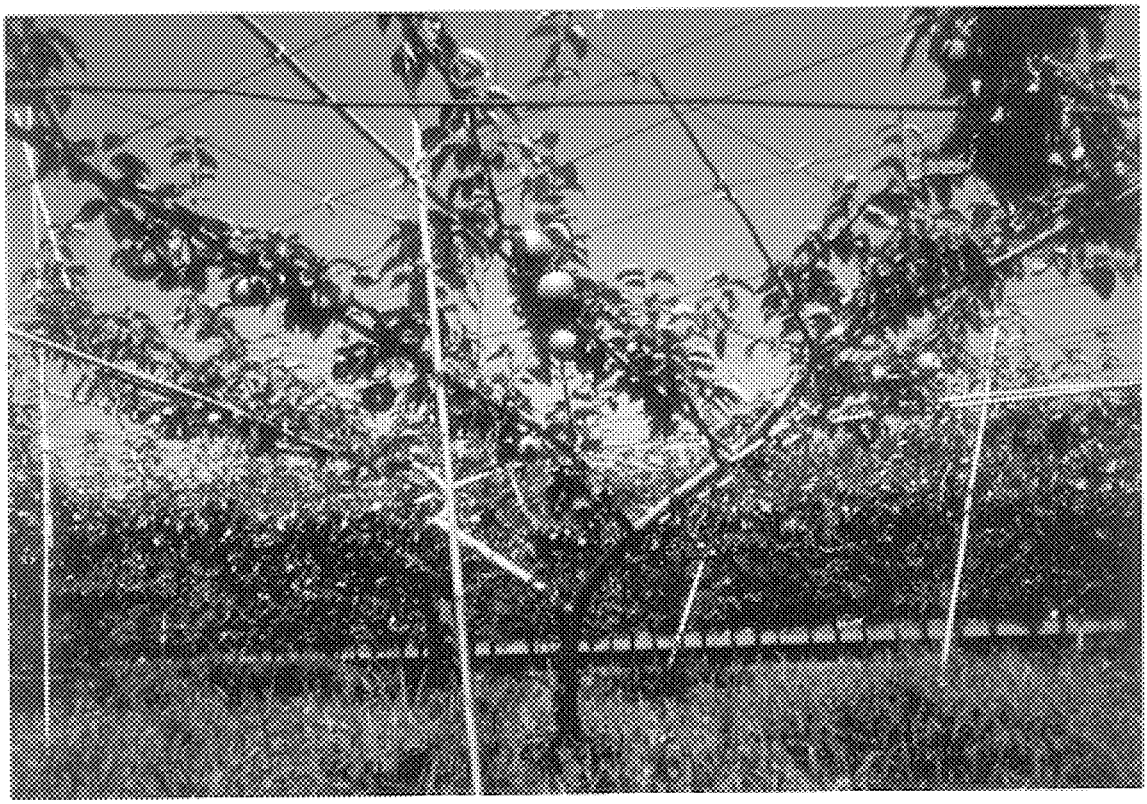
FIG. 1 is a photograph of the new cultivar, 'KOTOBUKI SHINSUI', as trained.
Figure 2:
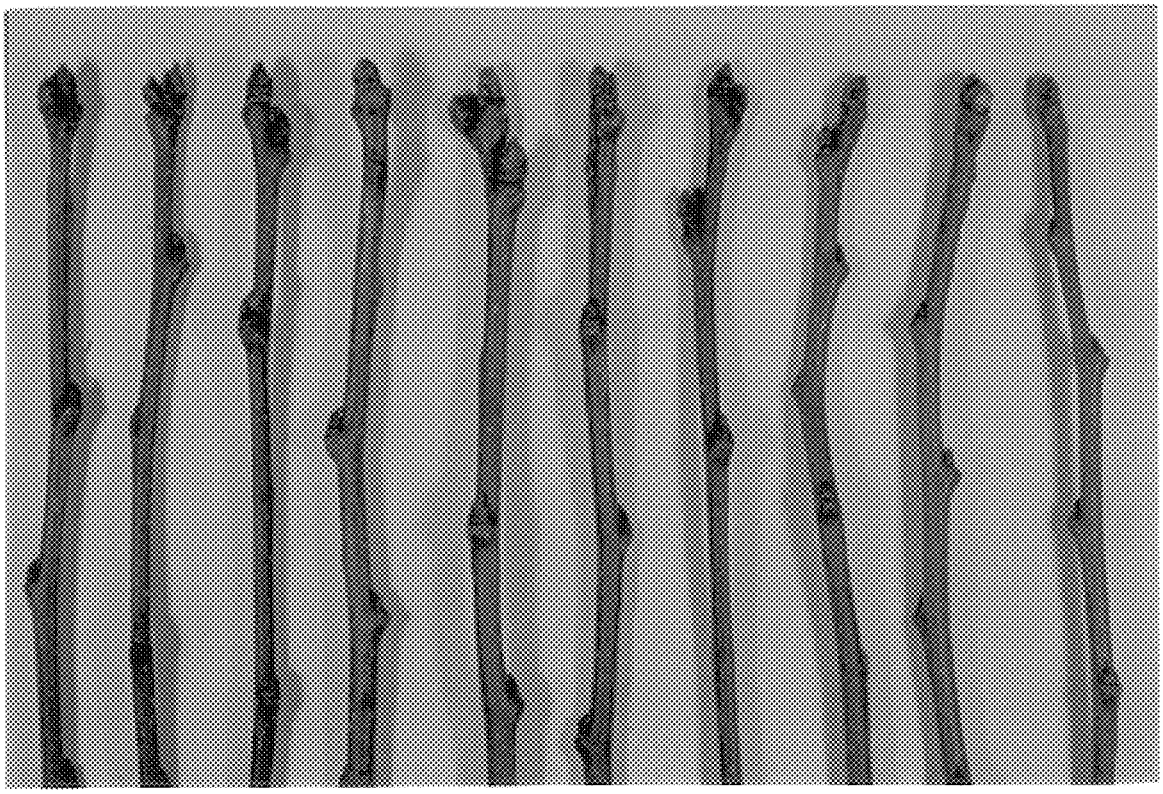
FIG. 2 is a photograph of the branches of 'KOTOBUKI SHINSUI'.
Figure 3:
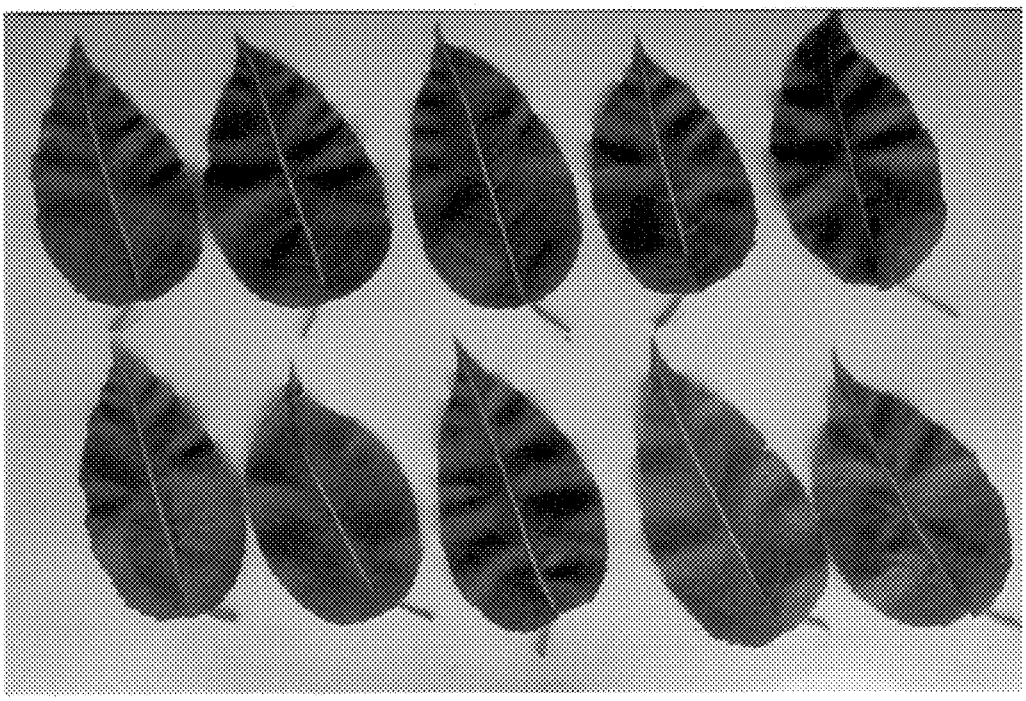
FIG. 3 is a photograph of the adaxial adult leaves of 'KOTOBUKI SHINSUI'.
Figure 4:
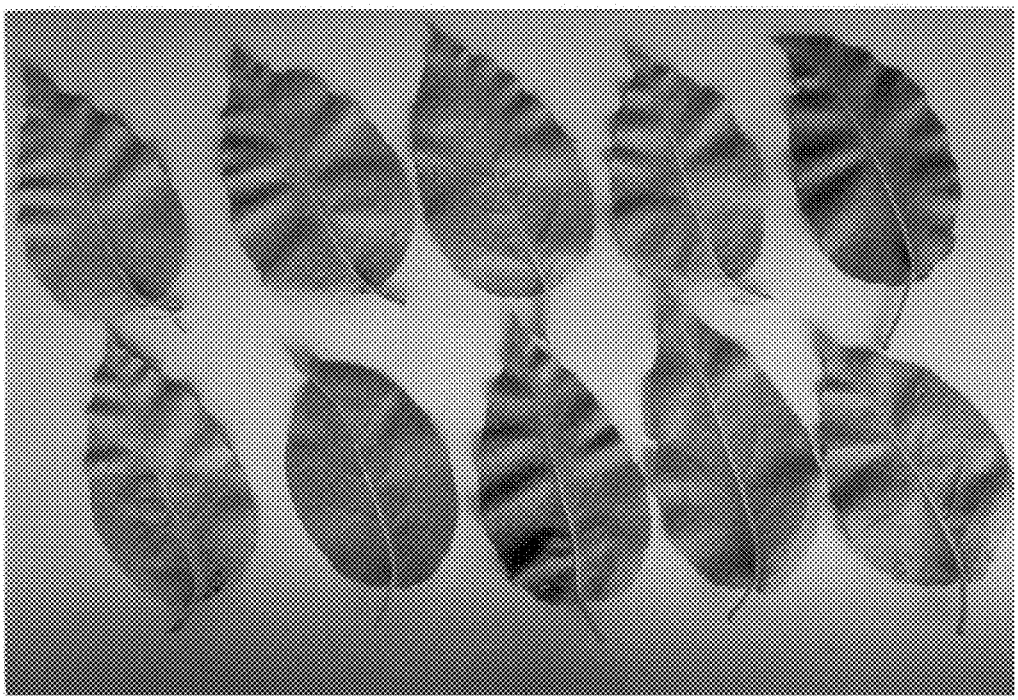
FIG. 4 is a photograph of the abaxial adult leaves of 'KOTOBUKI SHINSUI'.
Figure 5:
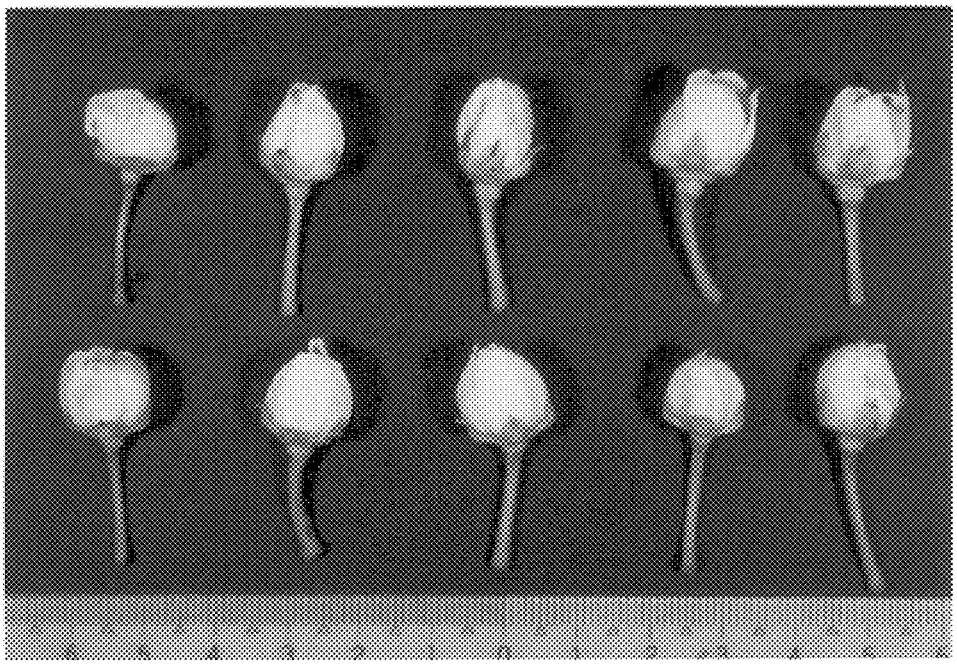
FIG. 5 is a photograph of the side view of the flowers of 'KOTOBUKI SHINSUI' in the bud stage.
Figure 6:
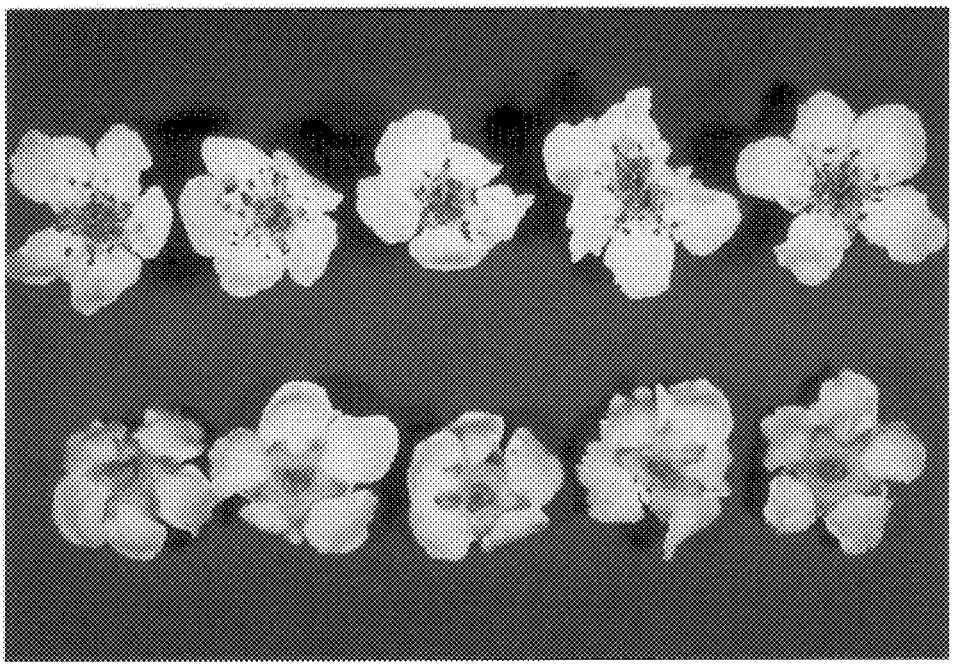
FIG. 6 is a photograph of the flowers of 'KOTOBUKI SHINSUI'.
Figure 7:
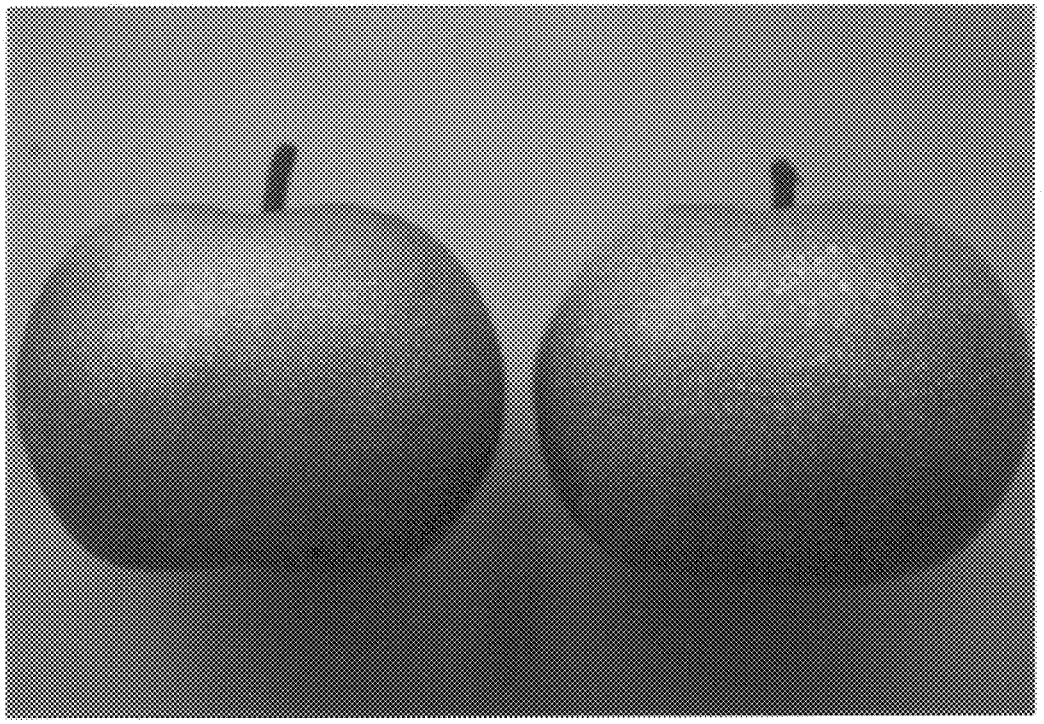
FIG. 7 is a photograph of the fruit of 'KOTOBUKI SHINSUI'.
Figure 8:
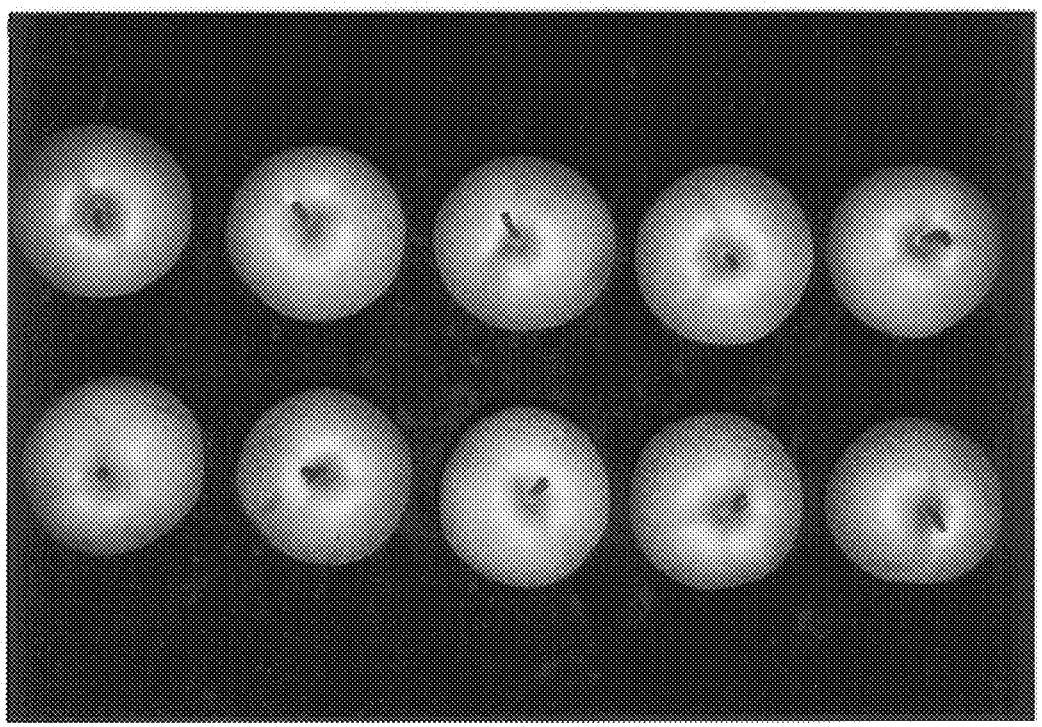
FIG. 8 is a photographic view of the stem end of the fruit of 'KOTOBUKI SHINSUI'.
Figure 9:
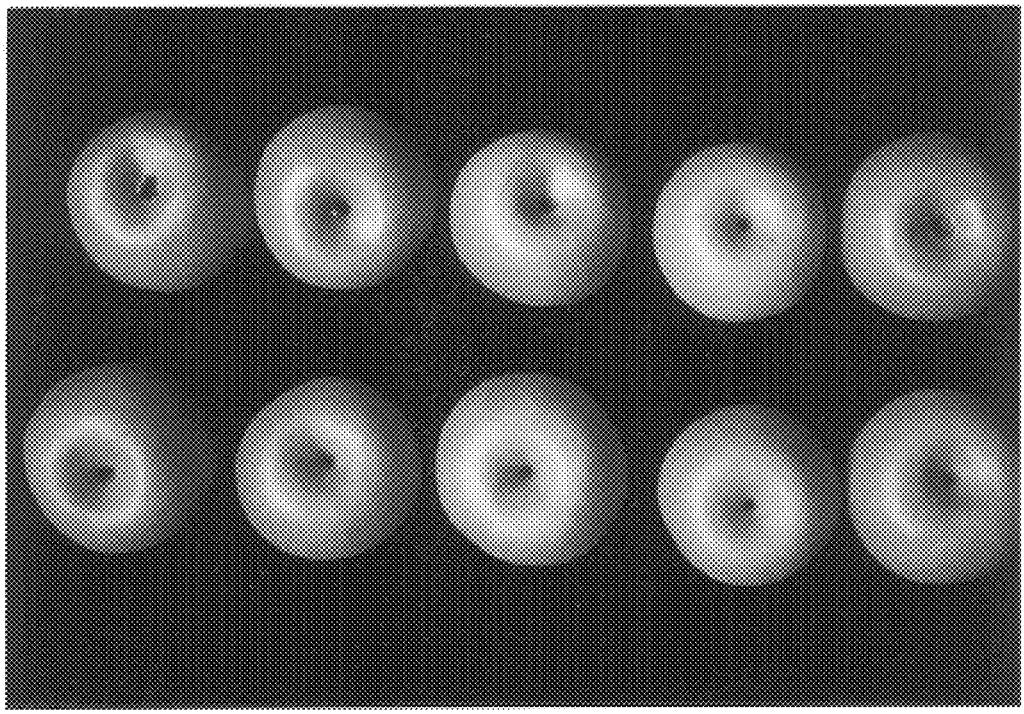
FIG. 9 is a photographic view of the blossom end of the fruit of 'KOTOBUKI SHINSUI'.
Figure 10:
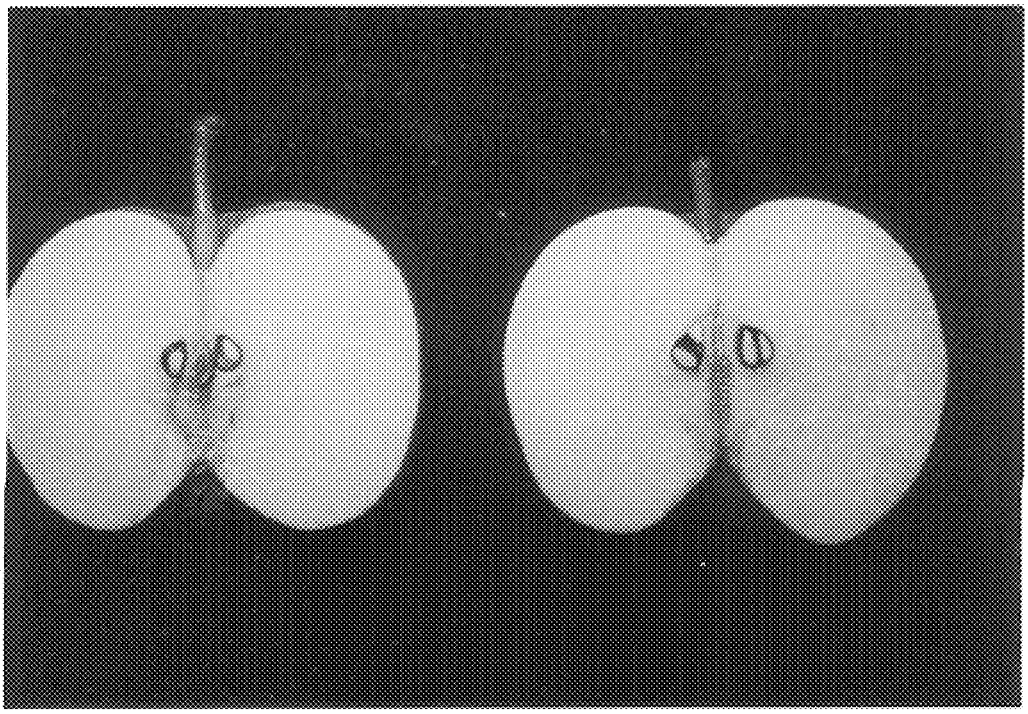
FIG. 10 is a photograph of a longitudinal sectional view of fruits of 'KOTOBUKI SHINSUI'.
Figure 11:
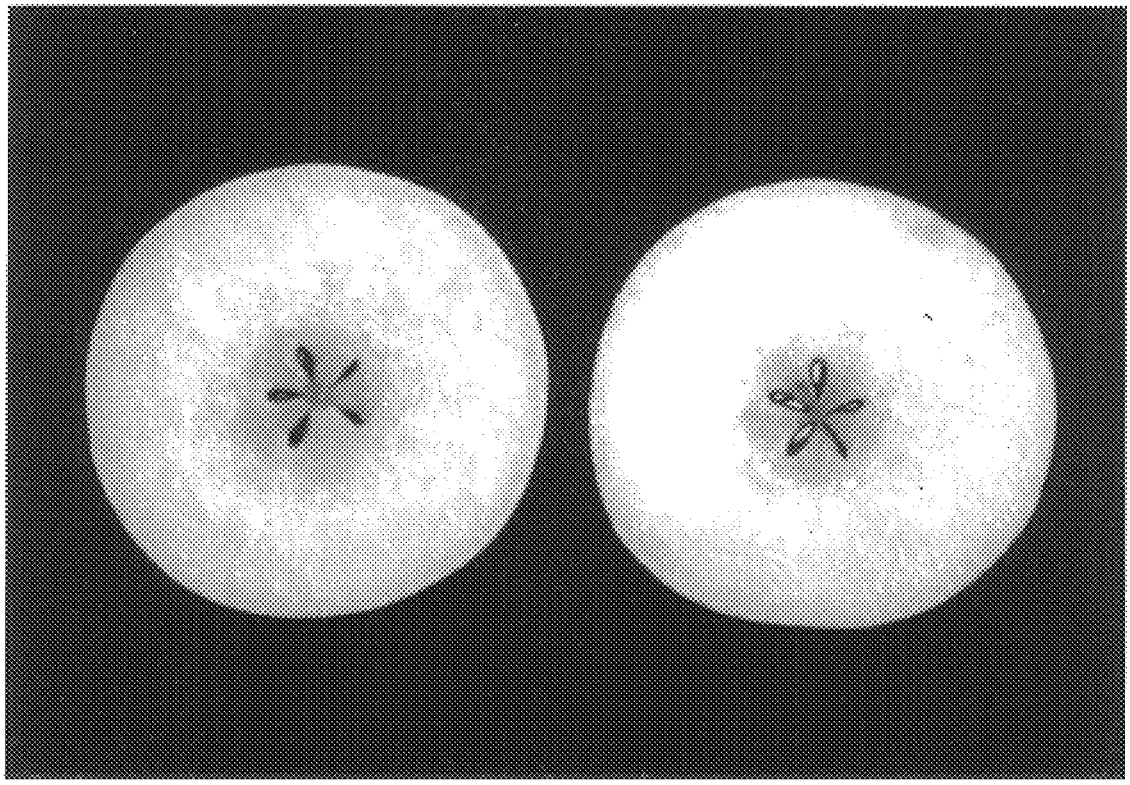
FIG. 11 is a photograph of a cross-sectional view of fruits of 'KOTOBUKI SHINSUI'.
Figure 12:
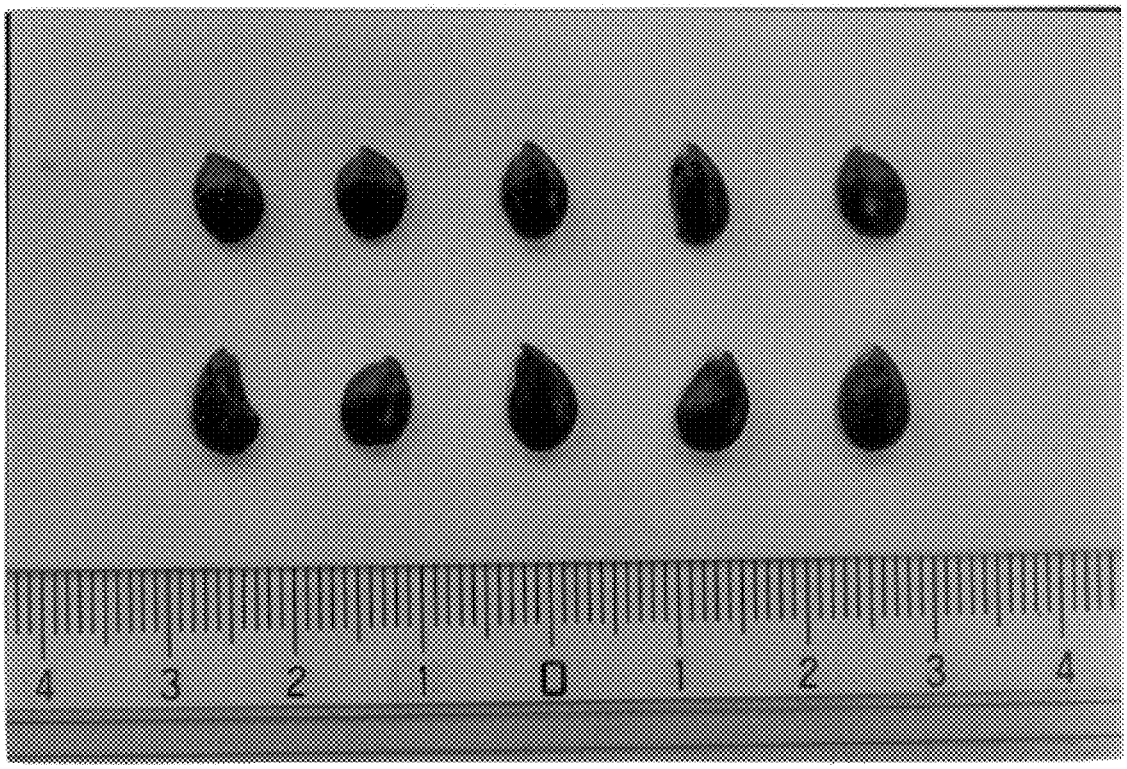
FIG. 12 is a photograph of the side view of seeds of 'KOTOBUKI SHINSUI'.

The characteristics of the new and distinct cultivar of Japanese pear tree 'KOTOBUKI SHINSUI' are as follows (In the following description, the color-coding is in accordance with The Royal Horticultural Society's R.H.S. Colour Chart):

Tree:

*Vigor.*—Strong; new shoot growth averaged 180 cm in 1999.

*Branch habit.*—Medium.

*Spurs.*—Many; in 1999 an average of 14.7 per meter of a branch.

*Number of axillary flower buds.*—Few.

*Time of bud break.*—Medium, around April 15th at Tottori prefecture, Japan.

*Production.*—Medium productivity.

*Cross-compatibility.*—Cross compatible with 'Chojuro' (unpatented) and 'Nijisseki', but incompatible with 'Kosui' and 'Shinsui'. The tree has low self-compatibility and is manually pollinated.

*Bark.*—The bark of the new and old wood is hard. The size of the lenticels of the new and old wood are medium, and density thereof is also medium (about 93 lenticels per 10 cm).

*Trunk surface.*—The color is R.H.S. Colour Chart Greyed-Orange 177A.

Branches (Shoot):

*Length.*—Medium.

*Thickness.*—Medium, about 9 mm.

*Length of internode.*—Short, about 3.7 cm.

*Color.*—R.H.S. Colour Chart Greyed-Brown 199B.

*Density of pubescence.*—Medium.

*Angle between leaf bud and shoot.*—Acute.

Leaves:

*Shape.*—Ovate.

*Size.*—Medium, (11 cm long by 7.1 cm wide).

*Color (adult leaves).*—R.H.S. Colour Chart 137A for adaxial leaves and R.H.S. Green 138D for abaxial leaves.

*Length of petiole.*—Short, about 2.2 cm.

*Thickness of petiole.*—Medium, about 2 mm.

*Color of young leaves.*—R.H.S. Red-Purple 60A.

*Density of pubescence of young leaves.*—Medium.

Flowers:

*Flower number in a flower cluster.*—Medium, about 8 flowers per cluster.

*Size.*—Medium, the average flower diameter is about 3.2 cm.

*Color.*—R.H.S. Red-Purple 57C corolla at early stages of blooming and fading to R.H.S. White 155D in later days, so that the color of the opened flower is white ( R.H.S. White 155D).

*Shape of petals.*—Round.

*Notch of petal margin.*—Medium.

*Number of petals.*—Slightly more than medium, 5.0 per flower on average.

*Color of anthers.*—R.H.S. Red-Purple 60C.

*Number of stamens.*—Slightly more than medium, 21.4 on average.

*Amount of pollen.*—High.

*Flowering time.*—Middle of the season.

*Flowering date and full bloom stage.*—Around April 17th and April 20th at the Tottori Prefecture, Japan. (Two days earlier than 'Kosui' and two days later than 'Hosui'). The approximate duration of bloom of the new cultivar at Tottori Prefectural Experiment Station (Tottori-ken) was from 7 to 9 days in 1992–1999.

Fruit:

*Size.*—294 g on average in 1992.

*Shape.*—Oblate.

*Color of skin (unbagged fruit).*—R.H.S. Small, Greyed-Orange 163A.

*Calyx.*—Almost all of the fruits are calyx deciduous, but some of the fruits are calyx perpetual.

*Size of dots on fruit skin.*—Medium.

*Density of dots on fruit skin.*—High.

*Color of dots on fruit skin.*—R.H.S. Gray-Yellow 162A.

*Color of flesh.*—R.H.S. Yellow-White 158C.

*Flesh.*—Between soft and medium and medium juicy. The firmness is about 4.7 lbs. according to Magness-Teller's hardness meter index.

*Length of peduncle.*—Medium.

*Thickness of peduncle.*—Thin.

*Color of peduncle.*—R.H.S. Yellow-Green 152A.

*Color of core.*—R.H.S. Yellow-White 158D.

*Shape of core.*—Short conical.

*Size of core.*—Ratio of transverse diameter of core to transverse diameter of fruit is medium, 25.4/84.6.

*Seed cells.*—Medium. 5.2 cells per fruit on average.

*Size of seeds.*—Medium, about 8 mm by 5 mm on average.

*Color of seeds.*—R.H.S. Black 202A.

*Shape of seeds.*—Oval.

*Taste.*—Highly sweet, the total sugar content of the fruit juice is about 13.6%, medium in acidity, pH 4.7, and no astringency.

*Bagging.*—The bagged fruit has a slightly fine appearance than the fruit that has not been bagged.

*Maturity.*—Ripening early in the season, e.g., August 15th–28th at the Tottori Prefecture, Japan.

*Productivity.*—The production of a 6-year old immature tree of the new cultivar was 9.6 kg/tree and the productivity of a 26-year old adult tree of 'Shinsui' was 126 kg/tree in 1998.

*Use.*—Suitable for dessert.

*Keeping quality.*—Can be kept for about 6 days at 20–25° C.

Figure 13:
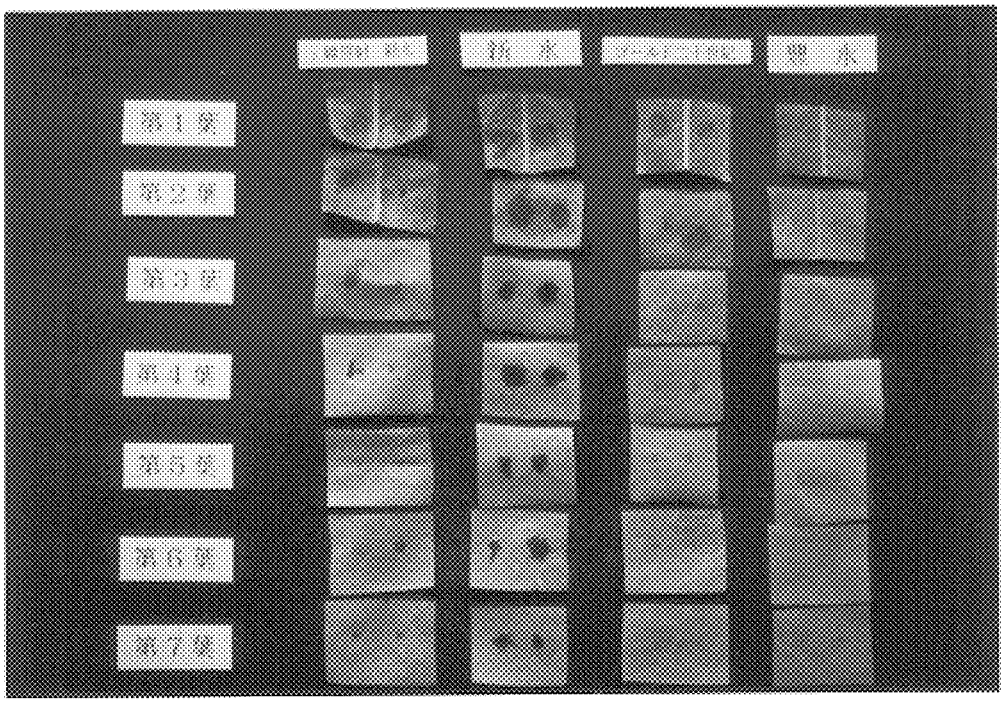
FIG. 13 is a photograph of leaf parts treated with AK toxin with a 1000-fold dilution. wherein seven leaves each were taken from 'KOTOBUKI SHINSUI', 'Shinsui', 'Gold Nijisseiki' (U.S. Plant Pat. No. 8,529), and 'Hosui' and placed in four columns. The four columns are, from left to right, 'KOTOBUKI SHINSUI', 'Shinsui', 'Gold Nijisseiki', and 'Hosui', respectively.
Figure 14:
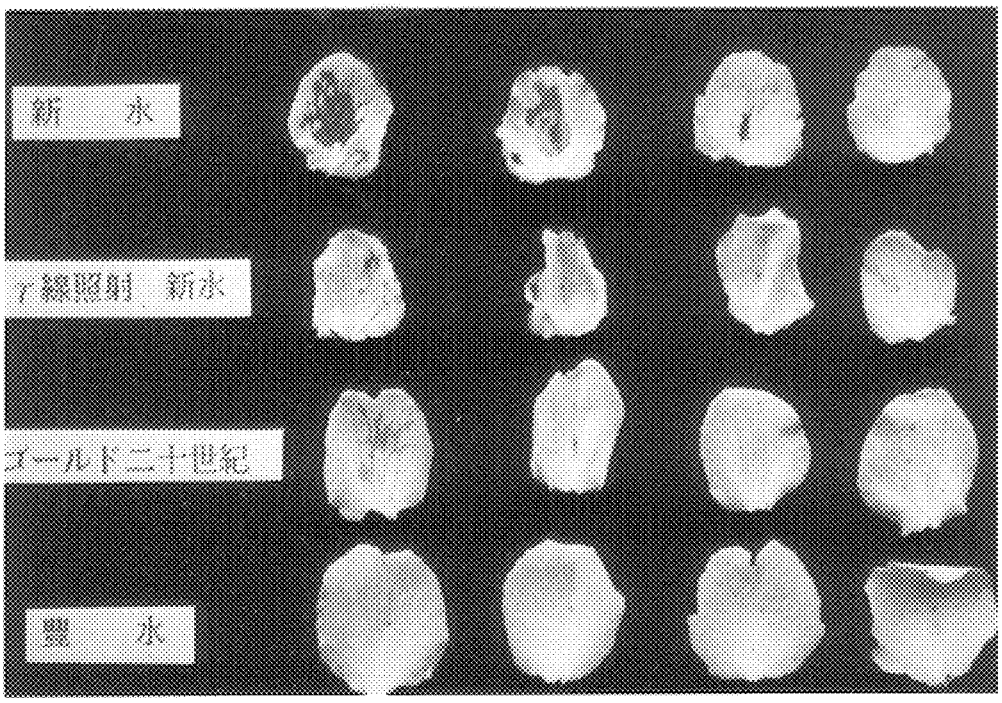
FIG. 14 is a photograph of petals of 'Shinsui' (the top row), 'KOTOBUKI SHINSUI' (the second row), 'Gold Nijisseiki' (the third row) and 'Hosui' (the bottom row); wherein in each row the first, second, third and fourth petals were treated with crude toxin with 500-fold dilution, crude toxin with 1000-fold dilution, crude toxin with 10,000-fold dilution and distilled water as a control, respectively.
Figure 15:
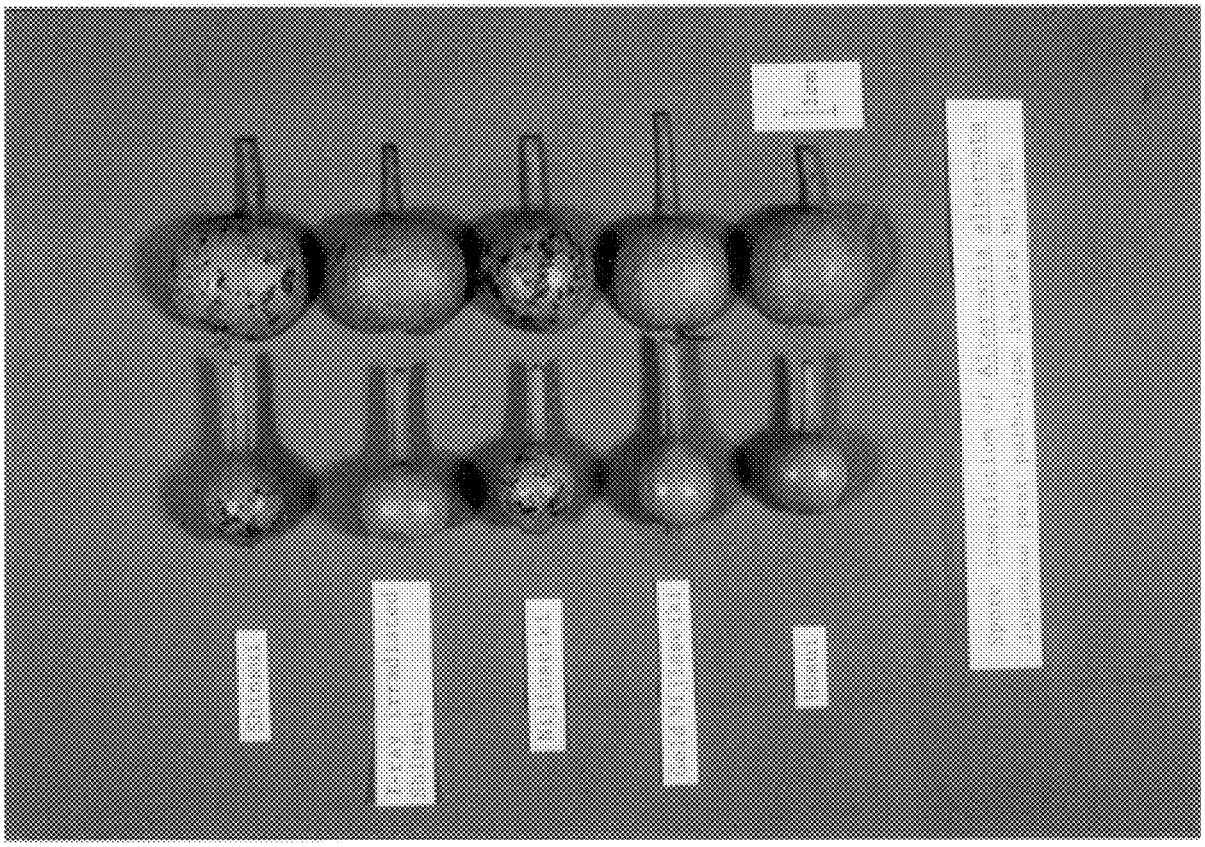
FIG. 15 is a photograph of young fruits after 30 days from flowering (the lower row) and 45 days from flowering (the upper row) of 'Shinsui', 'KOTOBUKI SHINSUI', 'Nijisseiki' (unpatented), 'Gold Nijisseiki' and 'Hosui', from the left to the right, respectively, about 24 hours after inoculation with spore of *Alternaria alternata* Japanese pear pathotype isolate ML-10E.
Figure 16:
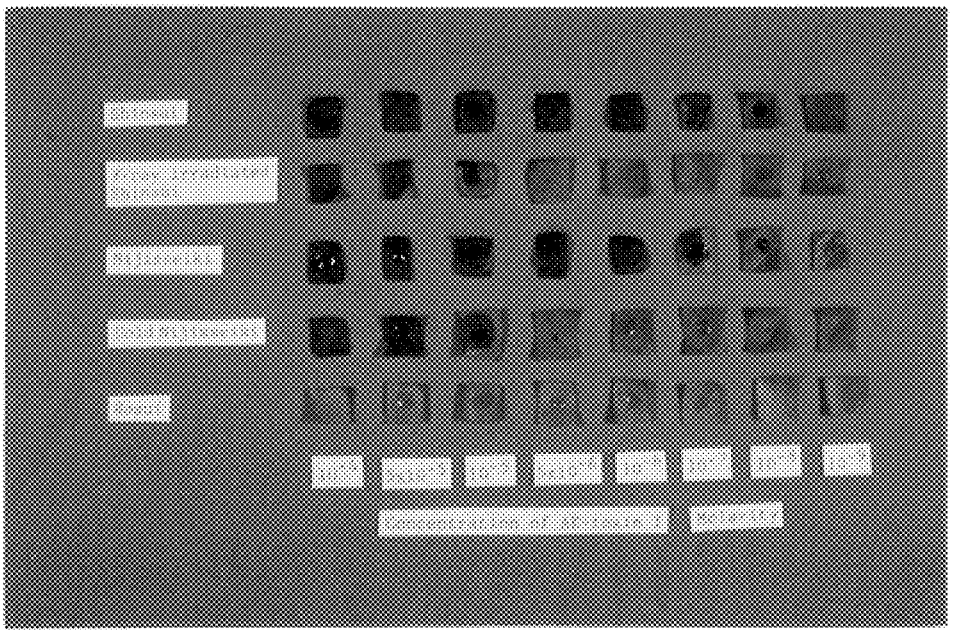
FIG. 16 is a photograph of parts of the fourth leaves of, from the top to bottom rows, 'Shinsui' 'KOTOBUKI SHINSUI', 'Nijisseiki', 'Gold Nijisseiki' and 'Hosui' treated with AK toxin at a concentration of $1\times10^{-4}$, $5\times10^{-5}$, $1\times10^{-5}$, $5\times10^{-6}$, $1\times10^{-6}$, $1\times10^{-7}$, $1\times10^{-8}$or $1\times10^{-9}$ M (from the left to right columns). It is clear that 'KOTOBUKI SHINSUI' is much more resistant to AK toxin than 'Shinsui' because the concentrations of AK toxin producing a similar blackening effect on the leaves differ by as much as two order of magnitude between 'KOTOBUKI SHINSUI' and 'Shinsui'.
Figure 17:
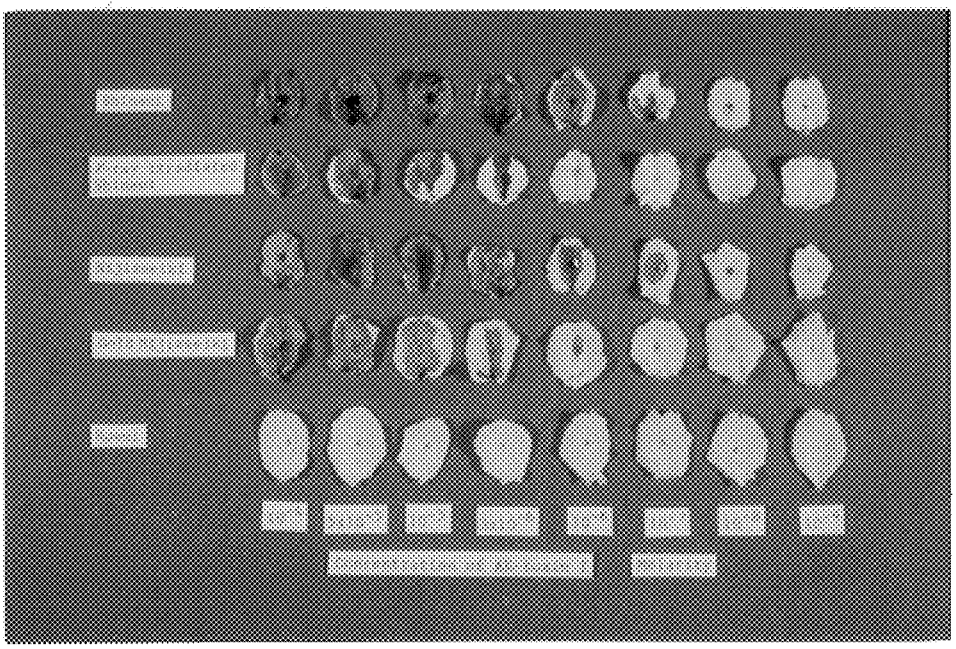
FIG. 17 is a photograph of petals of, from the top to bottom rows, 'Shinsui', 'KOTOBUKI SHINSUI', 'Nijisseiki', 'Gold Nijisseiki' and 'Hosui' treated with AK toxin at a concentration of $1\times10^{-4}$, $5\times10^{-5}$, $1\times10^{-5}$, $5\times10^{-6}$, $1\times10^{-6,}$ $1\times10^{-7}$, $1\times10^{-8}$ or $1\times10^{-9}$ M (from the left to right columns). It is clear that 'KOTOBUKI SHINSUI' is much more resistant to AK toxin than 'Shinsui' because the concentrations of AK toxin producing a similar dark browning effect on the petals of 'KOTOBUKI SHINSUI' and 'Shinsui' differ by at least one to one and a half order of magnitude.
Figure 18:
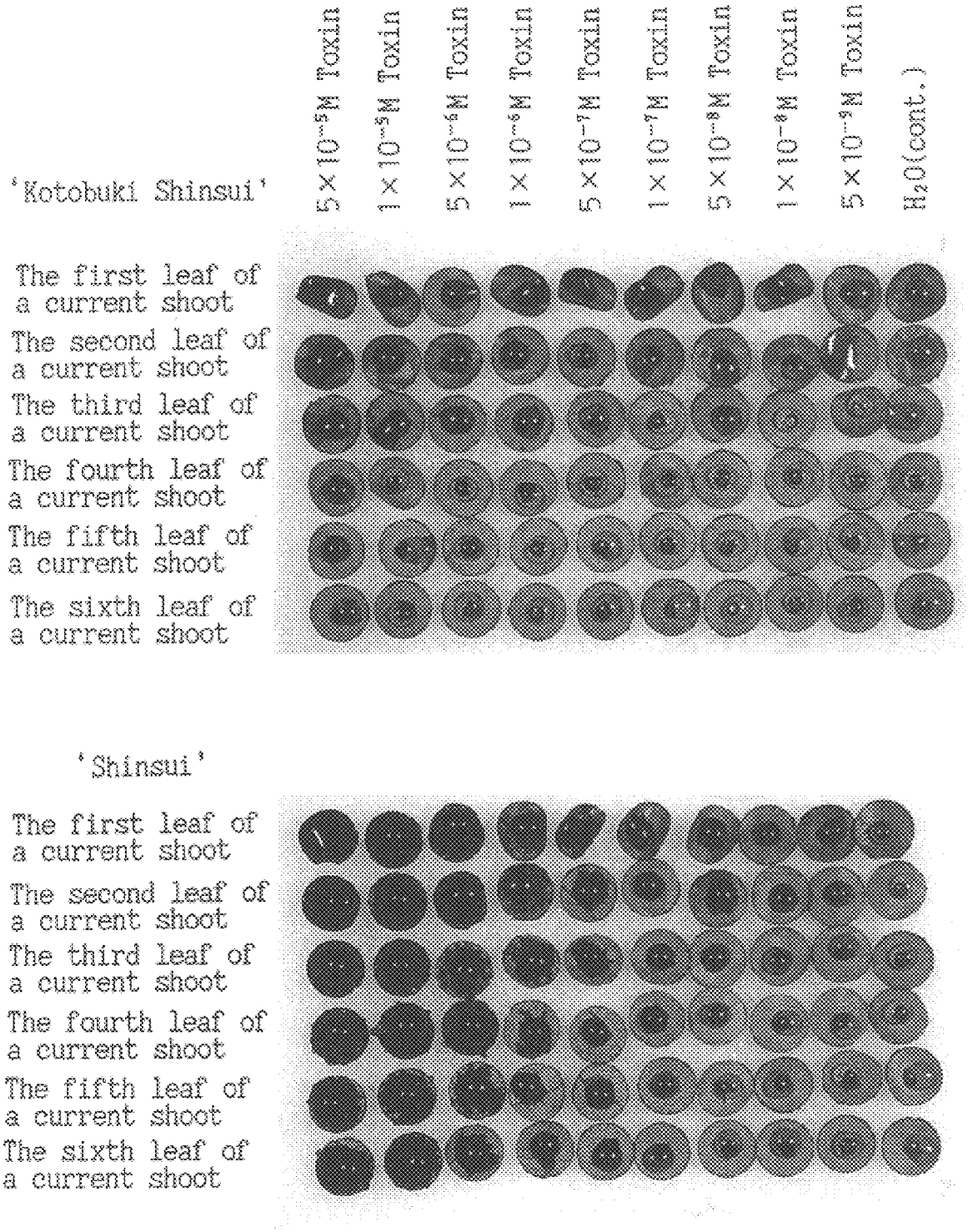
FIG. 18 illustrates the effects of AK toxin at different concentrations ranging from $5\times10^{-5}$ M to 5 $\times10^{-9}$ M or distilled water (from the left to right columns) on the first, second, third, fourth, fifth and sixth leaves of a current shoot of 'KOTOBUKI SHINSUI' (shown in the top panel) or 'Shinsui' (shown in the bottom panel). The degree of blackening depends on the concentration of the AK toxin and plant age in leaf number. It is claer that AK toxin resistance is much higher in 'KOTOBUKI SHINSUI' than in 'Shinsui' because the AK toxin concentrations producing a similar degree of blackening on the sixth leaves of 'KOTOBUKI SHINSUI' and 'Shinsui' differ by at least two and a half order of magnitude.

Resistance to Diseases:

The leaves, petals and young fruit (20, 30, 45 and 65 days after blooming) were inoculated indoors with a 100 to 1000 fold dilution od AK-toxin (culture filtrate of *Alternaria alternata* Japanese pear pathotype) or with black spot disease spores (atomizing inoculation with $5 \times 10^5$ spores/ml of strain 15A or *Alternaria alternata* Japanese pear pathotype isolate ML-10E) for a disease resistance test (see FIGS. 13–15).

Upon examination with black spot disease spore inoculation, the leaves of the original cultivar 'Shinsui' were entirely blackened, while blackening was found only on portions of the leaves of 'KOTOBUKI SHINSUI' (see Table 1). With AK toxin inoculation, treatment of the original cultivar 'Shinsui' with the toxin dilutions of 100 to 1000 fold resulted in rather extensive blackening on the affected parts of the leaves, but although 'KOTOBUKI SHINSUI' showed similar results using 100 to 500 fold dilutions, only slight blackening was found on the affected parts of the leaves using a 1000 fold dilution (see Table 2). Toxin treatment of the petals gave results similar to those for the leaves. In the spore inocultion test on the young fruit, widespread symptoms were found in the original cultivar 'Shinsui', while only small blackened areas were found in 'KOTOBUKI SHINSUI'.

Upon observation of the extent of onset of black spot disease in field cultivation, 'KOTOBUKI SHINSUI' is clearly more resistant than the original cultivar 'Shinsui', as 'Shinsui' exhibited symptoms in the young shoots and fruit with considerable fruit abscission due to black spot disease with non-bag cultivation, while 'KOTOBUKI SHINSUI' exhibited only slight symptoms and no fruit abscission.

Thus, the disease resistance of 'KOTOBUKI SHINSUI' is demonstrated to be stronger than that of 'Shinsui', although it is not a complete resistance, like 'Kosui' or 'Hosui', but rather a medium level of resistance similar to 'Gold Nijisseiki'.

The disease control methods used for the resistant cultivars 'Kosui' and 'Hosui' can be adequately applied as the disease control methods for the instant cultivar.

The present tree has no susceptibility to pear necrotic spot virus, and has minor susceptibility to pear scab, pear canker and physalospora canker.

Other cultural considerations:

*Cold resistance.*—Almost the same as that of other Japanese pears.

*Core breakdown.*—Absent.

*Watercore.*—Absent.

*Fruit cracking.*—Slightly apparent.

Culture.

Although the new cultivar has few axillary flower buds and many spurs, spurs have a tendency to form blind buds. However, this problem can be solved by adequate tree training and pruning methods.

The new cultivar of Japanese pear tree, 'KOTOBUKI SHINSUI', is cultivated and kept at the Institute of Radiation Breeding, National Institute of Agrobiological Resources, MAFF and Tottori Prefectural Experimental Station, Japan. 'KOTOBUKI SHINSUI' bears fruits every year.

Since the new cultivar, 'KOTOBUKI SHINSUI', has a strong resistance to black spot disease, and has excellent dessert quality, etc., the trees of the new cultivar can be conveniently and easily cultivated in various agricultural districts.

TABLE 1

Reaction with inoculation of black spot disease spore to the fourth leaf of a current shoot

| Variety line | Degree of blackening |
|---|---|
| Kotobuki Shinsui | ± |
| Shinsui | + |
| Hosui | – |
| Kosui | – |
| Nijjiseiki | + |
| Gold Nijjiseiki | ± |

–: No reaction
±: Portions of leaves were blackened
+: Leaves were entirely blackened Table 1 shows the response of the fourth leaf of a current shoot of 'KOTOBUKI SHINSUI', 'Shinsui', 'Hosui', 'Kosui', 'Nijisseiki' and 'Gold Nijisseiki' to an inoculation of black spot disease spore. According to Table 1, the inoculation produced only blackening in a portion of the fourth leaf of the current shoot of 'KOTOBUKI SHINSUI', but the inoculation made the fourth leaf of the current shoot of 'Shinsui' entirely blackened.

TABLE 2

Assay with inoculation of toxin to a leaf of a current shoot

| Variety line | Dilution Ratio ×100 Position of leaf 1 | 2 | 3 | 4 | ×500 1 | 2 | 3 | 4 |
|---|---|---|---|---|---|---|---|---|
| Kotobuki Shinsui | ++ | ++ | ++ | ++ | ++ | ++ | ++ | + |
| Shinsui | ++ | ++ | ++ | ++ | ++ | ++ | ++ | ++ |
| Hosui | – | – | – | – | – | – | – | – |
| Kosui | – | – | – | – | – | – | – | – |
| Nijjiseiki | ++ | ++ | ++ | ++ | ++ | ++ | ++ | ++ |
| Gold Nijjiseiki | ++ | ++ | ++ | ++ | ++ | ++ | ++ | ++ |

| Variety line | Dilution Ratio ×1000 Position of leaf 1 | 2 | 3 | 4 | Control (Distilled water) 1 | 2 | 3 | 4 |
|---|---|---|---|---|---|---|---|---|
| Kotobuki Shinsui | + | + | ± | ± | – | – | – | – |
| Shinsui | ++ | ++ | ++ | ++ | – | – | – | – |
| Hosui | – | – | – | – | – | – | – | – |
| Kosui | – | – | – | – | – | – | – | – |
| Nijjiseiki | ++ | ++ | ++ | ++ | – | – | – | – |
| Gold Nijjiseiki | + | + | ± | ± | – | – | – | – |

–: No reaction.
±: Slight blackening was observed at inoculation points.
+: Blackened portion slightly larger than inoculation points was observed.
++: Considerably larger blackened portion than inoculation points was observed.

Table 2 shows the response of a leaf of a new shoot of 'KOTOBUKI SHINSUI', 'Shinsui', 'Hosui', 'Kosui', 'Nijisseiki' and 'Gold Nijisseiki' to an inoculation of toxin. According to Table 2, the inoculation of the toxin with a 1/1000 dilution produced slight blackening at the inoculation points in the leaf of 'KOTOBUKI SHINSUI', while the inoculation of the toxin with the same degree of dilution produced a considerably larger blackened portion at the inoculation points in the leaf of 'Shinsui'.

We claim:

1. A new and distinct cultivar of *Pyrus pyrifolia* (Japanese pear) tree, substantially as herein illustrated and described, characterized by a significantly stronger resistance to black spot disease than 'Shinsui'.

* * * * *